United States Patent [19]

Cutler et al.

[11] Patent Number: 4,879,244

[45] Date of Patent: Nov. 7, 1989

[54] BIRTH CONTROL METHOD INVOLVING MONITORING OF AXILLARY ANDROSTENOL AND DEHYDROEPIANDROSTERONE

[75] Inventors: Winnifred B. Cutler, Haverford; George Preti, Horsham, both of Pa.; George R. Huggins, Parkton, Md.

[73] Assignees: Monell Chemical Senses Center; University of Pennsylvania, both of Philadelphia, Pa.

[21] Appl. No.: 5,240

[22] Filed: Jan. 20, 1987

Related U.S. Application Data

[62] Division of Ser. No. 695,053, Jan. 25, 1985, Pat. No. 4,670,401.

[51] Int. Cl.$^4$ .......................................... G01N 33/487
[52] U.S. Cl. ..................................... 436/65; 128/736; 128/738; 436/97
[58] Field of Search .......................... 436/65, 97, 906; 128/738, 736

[56] References Cited

U.S. PATENT DOCUMENTS

| | | | |
|---|---|---|---|
| 3,986,494 | 10/1976 | Preti et al. | 128/2 R |
| 4,010,738 | 3/1977 | Preti et al. | 128/2 R |
| 4,036,212 | 7/1977 | Karuhn | 436/92 |
| 4,119,089 | 10/1978 | Preti et al. | 128/2 R |
| 4,385,125 | 5/1983 | Preti et al. | 436/65 |

OTHER PUBLICATIONS

Frolich et al., "Serum Levels of Unconjugated Aetiocholanolone, Androstenedione, Testosterone, Dehydroepiandrosterone, Aldosterone, Progesterone and Estrogens During the Normal Menstrual Cycle," Acta Endocrinoogical, 81(3), 548–562, 1976.

Aedo et al., "Studies of the Pattern of Circulating Steroids in the Normal Menstrual Cycle," Acta Endocrinol., 84(2), 320–332, 1977.

Rance et al., "A Preovulatory Rise of Dehydroepiandrosterone in the Mare Measured by Radioimmunoassay," J. Steroid Biochem., 7(9), 677–681, 1976.

R. F. Vollman, "The Degree of Variability of the Length of the Menstrual Cycle in Correlation with Age of Woman", *Gynaecologia* 142(5):310–314 (Nov. 1956).

M. K. McClintock, "Pheromonal Regulation of the Ovarian Cycle: Enhancement, Suppression and Synchrony", *Pheromones and Reproduction in Mammals*, Edited by J. G. Vandenbergh, New York, Academic Press, pp. 113–149 (1983).

M. K. McClintock, "Estrous Synchrony: Modulation of Ovarian Cycle Length by Female Pheromones", *Physiol. Behav.*, 32:701–705 (1984).

M. K. Izard, "Pheromones and Reproduction in Domestic Animals", *Pheromones and Reproduction in Mammals*, edited by J. G. Vandenbergh, New York, Academic Press, pp. 253–281 (1983).

Izard et al., "*Priming Pheromones From Oestrous Cows Increase Synchronization of Oestrus in Dairy Heifers After PGF*-2αInjection" Reproduction Fertility, 66:189–196 (1982).

(List continued on next page.)

Primary Examiner—Michael S. Marcus
Assistant Examiner—Timothy M. McMahon
Attorney, Agent, or Firm—Washburn, Kurtz, Mackiewicz & Norris Woodcock

[57] ABSTRACT

A novel method of determining the onset of the fertile period of a human female is disclosed comprising the step of monitoring the axillary secretions of said female during the course of her menstrual cycle to determine variations in the concentration of androstenol or dehydroepiandrosterone sulfate. A first significant increase in the concentration of either of those compounds following the cessation of menses is indicative of the onset of the fertile period. In each case, a follicular phase peak occurs which exceeds by at least twice the concentration of those compounds present at any other time during the menstrual cycle. As a result, the monitoring of these compounds may act as reliable indicators predicting the occurrence of ovulation in five to seven days, and/or indicating contraceptive measures can still be taken to avoid pregnancy or sexual intercourse can promote fertility.

11 Claims, 1 Drawing Sheet

OTHER PUBLICATIONS

M. K. McClintock, "Menstrual Synchrony and Suppression", *Nature,* 229:244-245 (Jan. 22, 1971).

C. A. Graham et al., "Menstrual Synchrony in Female Undergraduates Living on a Coeducational Campus", *Psychoneuroendocrinology,* 5:245-252 (1980).

Rogel, "A Critical Evaluation of the Possibility of Higher Primate Reproductive and Sexual Pheromones", *Psychol. Bull.* 85:810-830, (1978).

D. M. Quadagno, "Influence of Male Social Contacts, Exercise and All-Female Living Conditions on the Menstrual Cycle" *Psychoneuroendrocrinology,* 6:239-244 (1981).

J. L. Veith et al., "Exposure to Men Influences in the Occurrence of Ovulation in Women", *Physiology & Behavior,* 31:313-315 (1983).

Russell et al., "Olfactory Influences on the Human Menstrual Cycle", *Pharmac. Biochem. Behav.,* 13(5):1-2 (1980).

J. N. Labows, "Human Odors—What Can They Tell Us?", *Perfumer and Flavorist,* 4:12-17 (1979).

J. J. Leyden et al., "The Microbiology of the Human Axilla and Its Relation to Axillary Odors", *J. Invest. Dermatol.* 77:413-416 (1981).

S. Bird et al., "Axillary 5αandrost-16-en-3-one, Cholesterol and Squalene in Men; Preliminary Evidence for 5αandrost-16-en-3-one Being a Product of Bacterial Action", *J. Steroid Biochem.,* 17:517-522 (1982).

S. Bird et al., "Measurement of 5αandrost-16-en-one in Human Axillary Secretions by Radioimmunoassay", *J. Endrocrinol.,* 85: 80-90.

B. W. L. Brooksbank et al., "The Detection of 5αandrost-16-en-3αol in Human Male Axillary Sweat", *Experientia,* 30:864-865 (1974).

R. V. Vollman, *The Menstrual Cycle,* vol. 7, (Major Problems in Obstetrics and Gynecology), edited by Emmanuel Freidman, M.D.

A. E. Treloar, "Variation of the Human Menstrual Cycle Through Reproductive Life", *Internl Journl of Fert.,* 12(1):77-126 (1967).

Clark et al., "Human Responses to Scent-Marking with the Putative Pheromone Androstenone" (unpublished manuscript) (1978).

W. Cutler, "Lunar and Menstrual Phase Locking", *American Journal of Obstetrics and Gynecology,* 137:834 (1980).

W. Cutler et al., "Infertility and Age at First Coitus: A possible Relationship" *J. Biosoc. Sc.,* 11:425-432 (1979).

W. Cutler et al., "Sexual Behavior Frequency and Menstrual Cycle Length in Mature Premenopausal Women", *Psychoneuroendocrinology,* 4:297-309 (1979).

W. Cutler et al., "Luteal Phase Defects: A Possible Relationship Between Short Hyperthermic Phase and Sporadic Sexual Behavior in Women", *Hormones and Behavior,* 13:214-218 (1979).

W. Cutler et al., "Sporadic Sexual Behavior and Menstrual Cycle Length in Women", *Hormones and Behavior,* 14:163-172 (1980).

W. Cutler et al., "The Psychoneuroendocrinology of the Ovulatory Cycle of Woman: A Review", *Psychoneuroendocrinology,* 5:89 (1980).

W. Cutler et al., "Sexual Behavior, Steroids & Hot Flashes are Associated During the Perimenopause", *Neuroendocrinology Letters,* 5:185 (1983).

J. N. Labows et al., "Steroid Analysis of Human Apocrine Secretion", *Steroids,* 34:249-258 (1979).

G. Preti et al., "Cyclic Changes in Volatile Acidic Metabolites of Human Vaginal Secretions and Their Relationships to Ovulation", *J. Chem. Ecol,* 1:361-376 (1975).

Abstract presented at the CRB Conference on Reproductive Behavior Jun. 10-12, 1984 at the University of Pittsburgh, entitled "Sex Frequency and Human Axillary Secretion Influence Fertile-Type Menstrual Cycles".

"Male Extract and Heterosexual Behavior Normalize the Menstrual Cycle of Women", Abstract, International Academy of Sex, Cambridge, England (Sep., 1984), Cutler et al.

A. R. Genazzani et al., "Possible Correlation Between Plasma Androgen Variations During the Menstrual Cycle and Sexual Behavior in the Human Female", *Chemical Abstracts,* vol. 91, 1978, Abstract No. 91:121339e, Proc. Serono Symp. 22 (Clin. Psychoneuroendo. Reprod. 419-435.

N. McCoy et al., "Relationships Among Sexual Behavior, Hot Flashes, and Hormone Levels in Perimenopausal Women", *Archives of Sexual Behavior,* 14(5):385-394 (1985).

Cutler et al., "The Medical Management of Menopause and Premenopause", Chapter 3, J. B. Lippincott Company, pp. 92-121 (1984).

"New Nose to Aid Fertility", *Daily News,* Aug. 14, 1984.

Bahn, *Basic Medical Statistics,* Chapter 8, "Review of (List continued on next page.)

OTHER PUBLICATIONS the Decision Making Process; the Error Risks", p. 86, (1972) Grune & Stratton, Inc.

Lee and Boot, *Acta Physiol. Pharmacol.*, Neerl, 5:213 (1956).

Cutler et al., "Sexual Behavior and Steroid Levels Among Gynecologically Mature Premenopausal Women", *Fertil. & Steril*, Apr. 1986.

Cutler et al., "Perimenopausal Sexuality", *Archives of Sexual Behavior* (in press).

C. C. Norris, "The Menopause", *American Journal of Obstet.*, 41:203–215 (1910).

Metcalf, "Incidence of Ovulatory Cycles in Women Approaching the Menopause", *Journal of Biosoc. Sci.*, 11:39–48 (1979).

Rutherford, "The Menopause", *N. Z. Med. J.*, 87:251–253 (1978).

Kupperman et al., "Contemporary Theory of the Menopausal Syndrome", *JAMA*, 171:1627–1637 (1959).

McCoy et al., "A Longitudinal Study of the Effects of Menopause on Sexuality", *Maturitas* 7:203–210 (1985).

Treloar, "Menstrual Cyclicity and the Premenopause", *Maturitas*, 3:249–264 (1981).

Cutler et al., "Sexual Behavior Frequency and Biphasic Ovulatory Type Menstrual Cycles", *Physiology & Behavior*, 34:805–810 (1985).

Cutler, et al., "Human Axillary Secretions Influence Women's Menstrual Cycles: The Role of Donor Extract from Men", *Hormones and Behavior*, 20:463–473 (1986).

Preti, et al., "Human Axillary Secretions Influence Women's Menstrual Cycles: The Role of Donor Extract of Females", *Hormones and Behavior*, 20:474–482 (1986).

ns, particularly to columns 1–5 of U.S. Pat. No. 4,119,089.

Perhaps the most popular and widely used method of estimating the time of ovulation relies upon the graphic recording of the waking temperature at basal conditions (hereinafter referred to as the BBT method). Using this method a dedicated woman with uniform daily habits can determine the time of ovulation within two days after its occurrence. In recording the basal body temperature, a rise in temperature is commonly associated with the beginning of the luteal phase, but can vary from the actual time of ovulation by as much as 72 hours. FIG. 1 of U.S. Pat. No. 4,119,089 illustrates a theoretical basal body temperature chart showing a biphasic cycle having a lowered body temperature during the follicular phase, and a sustained raised body temperature during the luteal phase.

Another technique which is commonly used to determine the time of ovulation in human females in the charting of concentrations of certain hormones appearing in the blood. In humans, a preovulatory rise in serum estrogens coupled with a sharp rise in luteinizing hormone (LH) levels as determined by radioimmunoassay of serially drawn blood samples, is perhaps the most accurate indicator of impending ovulation. Ovulation most likely occurs 12–24 hours after maximum LH levels. A subsequent persistent increase in levels of serum progesterone indicates that ovulation has occurred. Since these determinations are expensive and not widely available, clinical parameters such as BBT parameters are most often used to determine the time of ovulation.

The field of the present invention also relates to methods of predicting the onset of the fertile period. It is generally accepted that the maximum survival function of spermatozoa capable of fertilizing an ovum is approximately three days following coitus. Although theoretically any coitus prior to ovulation entails a certain risk of pregnancy, as a practical matter, abstinence from unprotected sexual intercourse for at least 3 days (preferably up to 5 days) prior to ovulation is generally considered sufficient to avoid pregnancy. It is generally recognized that a human ovum is (in vivo) fertilizable for about 12 hours and certainly for no more than 1 day following ovulation. The human fertile period, then, is made up of no more than 4 to 6 days out of the entire menstrual cycle. If it were possible to accurately predict this fertile period, in order to avoid pregnancy it would only be necessary to abstain from unprotected intercourse or use alternate birth control methods during that 4–6 day "fertile period" rather than for the entire menstrual cycle.

Notwithstanding the methods of the aforementioned related patents, the only technique yet widely used for "predicting" the fertile period of a female is the method which relies upon basal body temperature determination of ovulation in a plurality of preceding cycles to determine the expected time of ovulation for future cycles. This method is not really directed to ascertaining the precise fertile period for a given cycle, but rather is intended to identify a period during which coitus is statistically likely to produce pregnancy. Based on calendar records of 21,499 menstrual cycles experienced by 592 healthy women living in Switzerland, 9.75 of all menstrual cycles range in length from 6–23 days, 80.1% into the range from 24–34 days, and another 10.2% cover the remainder of menstrual cycles from 35 to 409 days in length. The modal cycle length of the

BIRTH CONTROL METHOD INVOLVING MONITORING OF AXILLARY ANDROSTENOL AND DEHYDROEPIANDROSTERONE

CROSS-REFERENCE TO RELATED PATENTS AND APPLICATIONS

This is a division of application Ser. No. 695,053, filed Jan. 25, 1985, now U.S. Pat. No. 4,670,401, issued June 2, 1987.

The present application is related to U.S. Pat. Nos. 3,986,494 entitled "Method for Predicting and Detecting Ovulation" (Preti and Huggins); 4,010,738, entitled "Method of Predicting and Detecting Ovulation" (Preti and Huggins); 4,119,089, entitled "Method of Predicting and Determining Ovulation by Monitoring the Concentration of Volatile Sulfur-Containing Compounds Present in Mouth Air" (Preti, Huggins and Tonzetich); and 4,385,125, entitled "Method Detecting Ovulation by Monitoring Dodecanol Concentration in Saliva" (Preti, Kostelc, Tonzetich and Higgins), each of which patents is hereby incorporated by reference as if fully set forth herein.

This application is further related to U.S. application No. 694,947, filed Jan. 25, 1985, entitled "The Use of Male Essence, Including Androstenol and Dehydroepiandrosterone Sulfate to Treat Luteal Phase Defects and Failure to Ovulate in Human Females", which application is also incorporated by reference as if fully set forth herein.

This application is also related to U.S. application No. 594,946, filed Jan. 25, 1985, entitled "Method Using Pooled Female Axillary Essence From Multiple Donors to Alter Menstrual Cycle Timing", which application is hereby incorporated by reference as if fully set forth herein.

BACKGROUND OF THE INVENTION

The present invention relates to the field of reproductive biology, and more particularly to methods used by reproductive biologists, gynecologists and/or obstetricians to predict in human females the probability that a given menstrual cycle type is presumptively fertile or infertile, the timing of the menstrual cycle, and/or the onset of the fertile period, the time of ovulation. The field of the present invention includes the field of detection and diagnosis of ovulation in human females through the detection of secondary characteristics occurring during or at the time of ovulation, and more particularly, to the identification and detection of such secondary characteristics as they appear in human females.

For many years there has been a need to detect and diagnose the precise time of ovulation in a given female mammal. It can be of great importance, for example, to pinpoint the time of ovulation to ensure that fertilization occurs or to prevent conception. Alternatively, it may be important for other medical reasons to diagnose ovulation.

To some extent, methods of diagnosing ovulation are disclosed in the above-identified related patents. Additionally, the occurrence of ovulation can be established with some certainty through various prior art methods. For a review of many of the known surgical, clinical, biochemical or hystological techniques for diagnosing ovulation, please refer to the descriptions appearing in the above-mentioned related patents and patent applicacycle of 28 days duration and the average cycle length amounts to 29.2 days. See "The Degree of Variability in the Length of the Menstrual Cycle in Correlation with Age of Woman", by R. F. Vollman, *Gynaecologia*, 142(5):310–314 (November 1956). Since this information is based upon past performance, and since the time of ovulation varies markedly between different individuals as well between cycles of a given individual, the period for abstinence must be long enough to considerably reduce the possibility of pregnancy. As explained in U.S. Pat. No. 4,119,089, taking into account the variability in menstrual cycle length, even the most regular women probably need to abstain from unprotected coitus for more than one-third of the total menstrual cycle in order to avoid pregnancy. Accordingly, a long felt need exists for methods of more accurately predicting or detecting the onset of the fertile period for a given cycle, such that coitus can be avoided, or other contraceptive methods employed, during the fertile period of that cycle.

The present invention also relates to the field of mammalian chemical communication, and more particularly to research involving mammalian pheromones. It has long been known that the estrus cycles of certain mammalian species are effected by pheromones and that their estrus cycles may be artificially manipulated. For examples, estrus cycles of rats can be manipulated through the use of odors collected form females during specific phases of the estrous cycle. See McClintock, M.K., "Pheromonal Regulation of the Ovarian Cycle: Enhancement, Suppression and Synchrony", *Pheromones and Reproduction in Mammals*, edited by J. G. Vanderbergh. New York: Academic Press, pp. 113–149 (1983) and McClintock, M. K., "Estrous Synchrony: Modulation of Ovarian Cycle Length by Female Pheromones"*Physiol. Behav.* 32:701–705 (1984). In addition, preovulatory cervical mucus mixed with water and sprayed into the noses of a group of female Holstein cows advanced and synchronized the time of estrous. See Izard, M. K., "Pheromones and Reproduction in Domestic Animals"*Pheromones and Reproduction in Mammals*, edited by J. G. Vandenbergh, New York: Academic Press, pp. 253–281 (1983) and Izard, M. K. and Vanderbergh, J. G., "Priming Pheromones From Oestrous Cows Increase Synchronization of Oestrus in Dairy Heifers After PGF-2 Injection". *J. Reprod. Fert.* 66:189–196, (1982). Notwithstanding these and other reports of elaborate pheromonal systems in other mammals there has been no experimental evidence that pheromonal systems operate in humans.

More recently a number of studies have suggested that possibility that human odors act in a manner analogous to primer pheromones in animals and alter reproductive endocrinology. Although anecdotal reports of aphrodesiacs are as old as modern civilization, the possibility that human reproductive biology can be altered by pheromones was not considered seriously until McClintock published a report in 1971 that menstrual synchrony occurred among certain women attending a predominantly female university. In "Menstrual Synchrony and Suppression", *Nature*, 229:244–245 (Jan. 22, 1971) McClintock reported that "social interaction" can have a strong effect on the menstrual cycle of women living together in a college dormitory. The McClintock study compared the dates of menstrual onset for roommates and close friends, and for living groups. McClintock reported that a significant increase in menstrual synchrony was found among roommates, among closest friends, and among roommates and closest friends combined. McClintock hypothesized that the synchrony could be due to some factor other than time spent with an individual such as the available food and/or synchrony of the moon. McClintock further speculated that synchrony might parallel the Whitten effect in mice in which suppression of oestrous in groups of females may be released by the introduction of a male mouse pheromone. McClintock suggested that synchrony might result from a pheromonal interaction of suppression among close friend groups, followed by a periodic release due to the presence of males on the weekend. McClintock stated:

"However, this would be insufficient to explain the synchrony which occurred among roommates and close friends but did not occur throughout the dormitory."

A further possible explanation advanced by McClintock was the awareness of menstrual cycles among friends, however a sample taken from the dormitory indicated that 47% were not conscious of their friends' menstrual cycles, and of the 53% who were, 48% were only vaguely aware. While McClintock was able to conclude that a significant factor in synchrony is that individuals in the group spend time together, McClintock was ultimately unable to state whether the mechanism underlying this phenomenon is pheromonal, mediated by awareness, or some other process, indicating that the question "still remains open for speculation and investigation". McClintock also explained:

"Exposure to males may not be the significant factor". It may be, for example, that those with longer cycles are less likely to spend time with males. However, many subjects spontaneously indicated that they became more regular and had shorter cycles when they dated more often. For example, one subject reported that she had a cycle length of six months until she began seeing males more frequently. Her cycle length then shortened to 4.5 weeks. Then, when she stopped seeing males as often, her cycle lengthened again. Whether this is due to a pheromone mechanism similar to the Lee-Boot effect in mice has yet to be determined."[Lee and Boot, Acta physiol. Pharamacol. Neerl., 5, 213 (1956)].

Subsequent investigators have also considered the effect on menstrual synchrony of females in different living conditions. In "Menstrual Synchrony in Female Undergraduates Living on a Coeducational Campus", *Psychoneuroendocrinology*, 5:245–252 (1980), Graham and McGrew report investigations of menstrual synchrony among female undergraduates living on a coeducational university campus. A significant trend toward synchrony was found for closest friends, but no significant effect occurred for neighbors or randomized pairs. Nor did any significant correlation emerge between cycle length, duration, duration of menstruation, or the amount and nature of social interaction with males. Graham and McGrew accordingly conclude that the amount of time individuals spend together, not similar living conditions, is the significant fact in synchrony. Graham and McGrew further conclude that the "how and why" of menstrual synchrony remain unknown, indicating that, as suggested by Rogel in "A Critical Evaluation of the Possibility of Higher Primate Reproductive and Sexual Pheromones", *Psychol. Bull.* 85:810–830 (1978), menstrual synchrony cannot be explained by any existing hypothesis other than a pheromonal one.

In 1981, Quadagno et al reported a tendency toward menstrual synchrony which was greatest between roommates and close friends. See Quadagno, D.M., Shubeita, H.E., Deck J. and Francoeur, D., "Influence of Male Social Contacts, Exercise and All Female Living Conditions on the Menstrual Cycle". *Psychoneuroendorcrinol.* 6:239-244 91981). Casual exercise performed regularly was associated with longer menstrual cycles whereas spending "social time" with a male was reported not to have any effect on the length of the menstrual cycle for the women in the study. Noting McClintock's finding that "women seeing males less than 3 times a week experience significantly longer cycles than women who spent time with males more than 3 times per week", Quadagno nonetheless confirms Graham and McGrew's findings that no significant correlation exists between cycle length and the amount and nature of social interaction with males.

Most recently, Veith et al have reported that exposure to men has the capacity to shorten the menstrual cycle in women. See "Exposure to Men Influence the Occurrence of Ovulation in Woman", *Physiology and Behavior* 31:313-315 (1983). Veith et al report that women who spent two or more nights with men during a 40 day period exhibited a significantly higher rate of ovulation as determined by basal body temperature charts than those spending no or one nights. Cycle length was not effected by sleeping arrangements, and the frequency of sexual intercourse was said to be unrelated to either cycle length or likelihood of ovulation. The mechanism underlying this phenomenon was reported to be "unknown", but was "conjectured" to be pheromonal in nature. Veith et al thus conclude that "a significant variable contributing to the likelihood of ovulation are the number of nights a woman spends in the same bed with a man". Veith et al further conclude that cycle length "was not influenced by this factor", noting that the "lack of replication of the earlier [McClintock] study concerning the lengthening of cycles in those women with limited exposure to males is surprising". Veith suggests that the naturalistic conditions resulting from subjects being enrolled in a coeducational institution may provide participants with sufficient exposure to men so that their cycle length would not be unduly increased.

A number of studies have investigated the possible effect of underarm perspiration on menstrual synchrony. In 1977, Russell, Switz and Thompson reported on the effects of using the female axillary sweat of a single, so-called "driver" female as a stimulus toward menstrual synchrony. See "Olfactory Influences on the Human Menstrual Cycle" presented at the meeting of the American Association for Advancement of Science, San Francisco, June 1977 and published in *Pharmac. Biochm. Behav.* 13(5):1-2 (1980). Russell et al had female volunteers rub on their upper lips cotton pads containing the perspiration odor of a particular donor female. After four months the menstrual onset dates of the volunteers were significantly closer to that of donor female than were the cycles of the control group who received the application but not the odor. The particular female donor subject had a history of a very regular menstrual cycle of 28 days and no significant history of menstrual problems. She had demonstrated a previous experience of "driving" another woman's menstrual cycle on three separate occasions over three consecutive years, did not use underarm deodorant nor shave under her arms. These data showed that the mean difference from onset of the menstrual cycle of the subjects from the donor was 9.3 days in the pretreatment month and 3.4 days in the post treatment month for the experimental group, and that this change showed statistical significance over the control group. Russel et al thus conclude that "odors from one woman may influence the menstrual cycle of another and that these odors can be collected from the underarm, stored as frozen samples, for at least short periods, and placed on another woman." The experiment was further said to support the theory that odor is a communicative element in human menstrual synchrony, and that at least a rudimentary form of olfactory control of the hormonal system is occuring in humans in a similar fashion to that found in other mammals.

As Russell et al noted, it is possible that volatile substances are transferred to the nose even though the subject has no awareness of them. It is also possible that the mechanism of transfer in the Russell et al study did not involve the nose at all, but diffusion of chemical compounds through the skin which may occur when the sample was placed on the subject's upper lip.

Underarm sweat comprises secretions of the apocrine, eccrine and sebaceous glands. Analyses of apocrine secretion have shown the presence of protein (10%), cholesterol (1%) and two androgen steroids: andosterone sulfate and dehydroepiandrosterone sulfate (0.2%). The apocrine secretion as collected at the skin surface is odorless; however, incubation with the resident skin bacteria results in an odor profile unique to that organism. The micrococci bacteria give an "acid odor" to the secretion which has been characterized by head space analysis as isovoleric acid. See Labows, J. N. 1979. "Human odors—what can they tell us!"*Perfumer and Flavorist* 4:12-17. The diptheroid bacteria give a similar head space profile but the observed odor is the more distinct "apocrine (human) odor" usually associated with the axillary areas.

Similar correlations of odor quality and bacterial populations were found in vivo. The axillary microflora of 229 subjects have been characterized quantitatively and their results correlated with the type of donor found. Micrococcaceae were present in all subjects and were the dominant organism when a faint or acid odor was noted. The aerobic diptheroids were found in 85% of the males and 66% of the females and were associated with a pungent, apocrine odor. There were no significant differences related to handedness or presence of axillary hair. See Leyden, J. J., McGinley, K. J., Hoelzle, E., Labows, J. N. and Kligman, A. M. 1981, "The Microbiology of the Human Axillae and its Relation to Axillary Odors", *J. Invest. Dermatol.* 77:413-416.

The "apocrine odor" is similar to that of androst-16-en-3-one. See Labows, J. N. 1979, supra. Neither this steroid nor androst-16-en-3-ol, a musky odorant are present in original odorless secretion but they have been shown to be present in axillary sweat. See Bird, S. and Gower, D. B. 1982, "Axillary 5-androst-16-en-3-one, Cholesterol and Squalene in Men: Preliminary Evidence for 5-androst-16-en-3-one Being a Product of Bacterial Action". J. Steroid Biochm. 17:517-522; Bird, S. and Gower, D. B., "Measurement of 5-androst-16-en-one in Human Axillary Secretions by Radioimmunoassay", J. Endorcrinol. 85:80-90; and Brooksbank, B. W. L., Brown, R. and Gustafsson, J. A. 1974, "The Detection of 5-androst-16-en-3-ol in Human Male Axillary Sweat", *Experientia* 30:864–865. In experiments in which axillary bacteria where incubated with sterile apocrine sweat, typical pungent malodor was produced only with aerobic diptheroids. This included both isovoleric acid and another component which was pungent. The odor is similar in character to androst-16-en-3-one and this material has been detected on axillary pads using radio-immunoassay procedures. See Bird, S. and Gower D.B. supra. Studies of extracts of odorous cultures of diptheroids grown on apocrine secretion by GC/MS as yet have not revealed detectable levels of androstenone. It is reasonable to assume, however, that further studies will reveal them since they are detected in axillary washings. See Personal Communication, 1984. Dr. J. N. Labows, Monell Chemical Senses, Center.

Apart from the above-mentioned data, Graham et al describe the remaining evidence for pheromonal communication of a human female's hormonal status as being "largely circumstantial and fragmentary". For example, Graham et al cite work on short-chain fatty acids in human vaginal secretions; vaginal odors; odor discrimination studies; effects of alleged human pheromonal preparations on subject performance; and scent-marking experiments in public places using androstenone, a mammalian pheromone, which is said to alter spontaneous behavior. See for example, Clark, Klassnick and Watson, "Human Responses to Scent-Marking with the Putative Pheromone Androstenone" (1978) (unpublished manuscript cited in Graham et al supra).

In addition to the above, numerous publications discuss various factors such as lunar synchrony which may effect the length of the human menstrual cycle. See "The Menstrual Cycle" by Rudolph V. Vollman, M. D., Vol. 7, *Major Problems in Obstetrics and Gynecology,* edited by Emmanual A. Freidman, M. D.; Treloar, "Variation of the Human Menstrual Cycle Through Reproductive Life", *International Journal of Fertility,* 12(1):77–126 (1967). More recently, Winnifred Berg Cutler has reported upon the relationship between the lunar and menstrual cycle phases. See "Lunar and Menstrual Phase Locking", by Winnifred Cutler, *American Journal of Obstetrics and Gynecology* 137:834 (1980). In this study, reference is made to data showing the mean and median of sample menstrual cycle data to be 29.5 days, and notes the coincidence of this cycle length and the 29.5 day lunar cycle. Cutler has noted that 98% of the cycles of 29.5±1 day in length are ovulatory, and has suggested that ovulation may frequently occur during the new moon part of the cycle.

In addition to the factors discussed above, sexual behavior has often been discussed as a factor which contributed to the rhythm of the human cycle and subsequent fertility. Cutler has published extensively on the possible interrelationship between infertility and first coitus, sexual behavior frequency and menstrual cycle length, short hyperthermic phases and sporadic sexual behavior in woman, and relationships between estrogen level, hot flashes and sexual behavior in perimenopausal woman. See Cutler et al "Infertility and Age at First Coitus; A Possible Association", *J. Biosoc. Sci.* 11: 425–432 (1979); Cutler et al, "Sexual Behavior Frequency and Menstrual Cycle Length in Mature Premenopausal Women", *Psychoneuroendocrinology* 4:297–309 (1979); Cutler et al, "Luteal Phase Defects: A Possible Relationship Between Short Hyperthermic Phase and Sporadic Sexual Behavior in Women", *Hormones and Behavior* 13:214–218 (1979); Cutler et al, "Sporadic Sexual Behavior and Menstrual Cycle Length in Women", *Hormones and Behavior* 14:163–172 (1980); Cutler et al, "The psychoneuroendocrinology of the Ovulatory Cycle of Woman, A Review", *Psychoneuroendocrinology* 5:1980; and Cutler et al, "Relationships Between Estrogen Level, Hot Flashes and Sexual Behavior in perimenopausal Women", *Neuroendocrinology Letters* 5:185 (1983).

In addition to the Vollman and Treloar studies discussed above, which clearly suggest that women whose cycles approach a 29 day span have the highest likelihood of a fertile cycle, Cutler et al have demonstrated that women who have regular weekly, heterosexual activity have menstrual cycles of about 29 days, whereas women who either have sporadic sexual activity or who are celibate tend to have a higher frequency of aberrant length cycles (25 or less or 34 or more days). These studies suggest that leuteal phase defects (shortened hyperthermic phases) and sporadic sexual activity in the luteal phase are associated in a population of infertility patients. Delayed age of first coitus is also associated with a higher frequency of subsequent infertility.

Even more recently, Cutler et al have evaluated whether self stimulation (masturbation), coitus, and or heterosexual genital stimulation by a man without coitus, could be differentiated in terms of their relative association to fertility. In this study presumptive fertility (P. fertility) was evaluated by the menstrual cycle length and by analysis of basal body temperature charts. It was found that weekly heterosexual behavior is consistently associated with menstrual cycle lengths of 29.5±3 days and that self stimulation behavior does not show a similar association between weekly behavior and circa 29 day menstrual cycle lengths. Women who report regular weekly sex with men are found to have a greater incidence of presumptively fertile menstrual cycles than those who report sporadic sexual activity. In the Cutler et al study the chief problem associated with less frequent sexual activity is less a failure to ovulate but rather a short luteal phase. A fertile menstrual cycle requires both an ovulation and an adequately long luteal phase to ensure sufficient time and steroid output to prepare the endometrium for implantation. The Cutler et al study shows that sexually active women who have regular, stable patterns of sexual activity have significantly more fertile type cycles than women of the same age who have sporadic patterns of sexual activity. The hypothesis that normalization of the menstrual cycle is due to something more than genital stimulation, but requires the presence of a male partner, is consistent with the suggestions of McClintock, the data of Quadagno, and numerous studies and observations conducted with non-human primates and other mammals, some of which suggest the presence of a male or his odors are important in regulating cyclicity and/or fertility.

The influence of mammals or their odors on the estrous cycles of other female conspecifics has been well-documented in recent studies employing infra-human mammals. See McClintock, M. K. 1983, supra., McClintock, M. K. 1984, Izard, M. K. 1983, supra., and Izard, M. K. and Vandenbergh, J. G. 1982, supra. For example, the estrous cycle of rats can be manipulated through the use of odors collected from females during specific phases of the estrous cycle. In several rodent species, exposure to the odors of urine or cage bedding or males can promote estrous or stimulate ovulation. In some infra-human primates, males can influence cycle length. Female baboons denied a mating showed significantly longer cycles and rhesus monkeys showed a summer amenorrhea two to four months after a male decrease in sexual potency.

Notwithstanding what is known on this topic, the problems of unwanted fertility and unwanted infertility remain among the most important of human concerns. Since a reasonable percentage of infertility may stem from conditions reflected in menstrual cycles of aberrant lengths, methods for adjusting the lengths of those menstrual cycles have a good likelihood of creating presumptively fertile 29.5±3 days cycles. Similarly, for those women choosing to avoid pregnancy, the provision of a physiologically compatible method for stimulating infertile-type cycles would be of utmost utility. Finally, improved methods for regulating the timing of the menstrual cycle could improve the predictability of the occurrence of the fertile period and/or menstruation and expand the range of therapeutic possibilities for addressing both fertility and infertility problems.

SUMMARY OF THE INVENTION

A novel method of determining the onset of the fertile period of a human female, and of predicting the time of ovulation in that female, is provided which comprises the step of monitoring the axillary secretions of that female during the course of her menstrual cycle to determine variations in the concentration of androstenol or dehydroepiandrosterone sulfate. First significant increases in the concentration of either of these compounds following the cessation of menses is indicative of the onset of the fertile period, and is predictive of ovulation in five to seven days.

In accordance with the preferred embodiment of the present invention, samples of axillary secretions of the subject female are collected periodically during her menstrual cycle beginning at the cessation of menses. This monitoring comprises determining the concentrations of androstenol or dehydroepiandrosterone sulfate in said samples, for the purpose of determining at least a four fold, preferably at least a ten fold increase in the concentration of either of these compounds as compared to their base levels immediately following menses. In each case, a follicular phase peak is indicative of the onset of the fertile period.

In accordance with the preferred embodiment method, indicator means is provided for qualitatively and quantitatively responding to variations in the concentration of androstenol or androsterone. Collected samples of the axillary secretions may be tested by the indicator means, which may be a gas chromatograph/mass spectrometer or a radioimmunoassay (RIA) test, to determine the concentration of the subject compound. Although daily collection is preferred, it may be possible to obtain indicative results by conducting periodic collections as infrequently as once every four days during the follicular phase of the menstrual cycle. However, the accuracy of the prediction of the onset of the fertile period is somewhat dependent upon the periodicity of the sampling procedure.

The present invention further provides improved birth control methods wherein the aforementioned procedures are combined with known contraceptive methods to facilitate their use beginning at the onset of the fertile period until at least about one day following the expected time of ovulation. In accordance with this birth control method, an additional step of determining the presumptive time of ovulation may be employed. This additional method may be clinical method, such as the interpretation of a basal body temperature chart, or a chemical method, such as the determination of a peak in the concentration of a compound which is indicative of the time of ovulation. A peak in the circulating blood levels of luteinizing hormone, or in the concentration of dodecanol in the female is saliva, or of certain volatile sulfur containing compounds in mouth air, or in the concentration of lactic acid, acetic acid, or urea found in that woman's vaginal secretions may be used as a presumptive ovulation indicator.

The reliability of such a birth control method may be further improved by improving the regularity of a woman's menstrual cycle. For example, the menstrual cycle of the human female may be adjusted by exposing the nasal region of that female to at least a portion of the axillary secretions of a human donor, as described in connection with the aforementioned related patent applications, which have been incorporated herein by reference. Such axillary secretions collected from one or more human males will, for example, tend to induce regular menstrual cycles having lengths of about 29.5±3 days. Alternatively, axillary secretions from at least one other human female selected in accordance with her known menstrual cycle history may act to adjust or disrupt the expected menstrual cycle of that female. In the former instance, the regularity of the induced cycle will improve the reliability of fertile period and ovulation indicators, whereas in the latter the disrupted menstrual cycle will itself tend to prevent pregnancy.

Accordingly, a primary object of the present invention is the provision of improved methods for determining the onset of the fertile period of a human female.

A further object of the present invention is the provision of a novel method for predicting the presumptive time of ovulation of that human female.

A further object of the present invention is the provision of an improved birth control method.

Still a further aim of the present invention is the provision of a method of improving the reliability of existing birth control methods which rely upon the sporadic use of contraceptive methods, materials or devices during a portion of the menstrual cycle of the human female.

These and other objects of the present invention will become apparent from the following, more detailed description.

DESCRIPTION OF THE PREFERRED EMBODIMENTS

Figure 2:
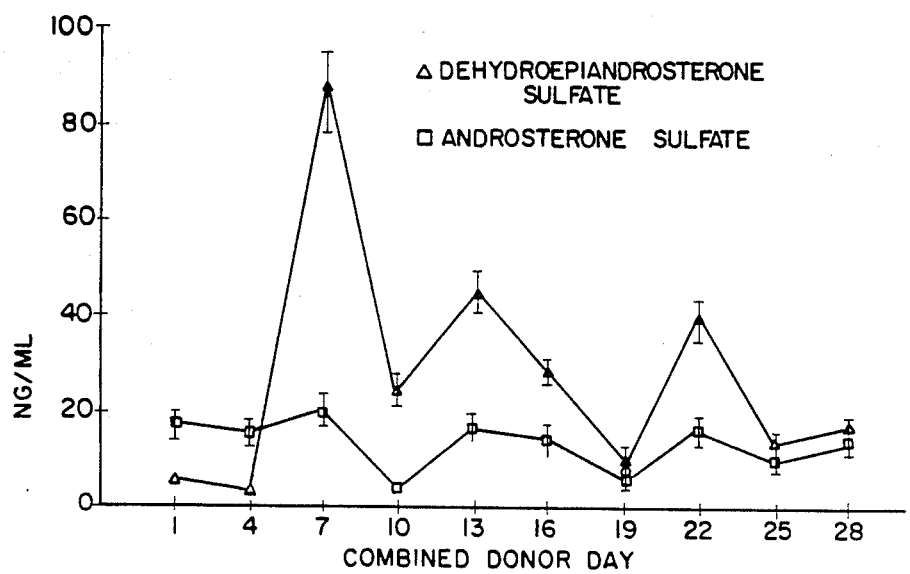
FIG. 2 is a graph of the concentration in nanograms per milliliter, of androstenol for samples of axillary extracts pooled from five women donors, as determined over the course of the menstrual cycle.

The present invention is predicated upon the finding that androstenol, and/or dehydroepiandrosterone sulfate exhibit distinctive cycling behaviors during the course of a woman's menstrual cycle, and that by monitoring the concentrations of either or both of these compounds, it is possible to determine the onset of the fertile period of that human female and/or to predict by five to seven days the time of ovulation.

Support for the above-stated conclusions comes from a study in which axillary secretions were collected from five female volunteer donors recruited from amongst co-workers and members of the community. All had the following characteristics: they were engaged in a heterosexual relationship; they had large numbers of lipophilic diptheroids in their axillary region, and for the duration of the experiment they did not use deodorant, deodorant soaps or perfumes in the axillary region; and they washed each morning with only Ivory soap.

Secretions were collected on 4"×4" cotton pads which had previously been extracted, autoclaved, dried and wrapped in solvent extracted aluminum foil. Each donor wore a pad in each axilla three times a week during a convenient six-to-nine hour periods. After removal, pads were immediately frozen in acid/solvent cleaned glass jars and stored at −60° C. until extraction, approximately one year later. Each donor collected secretions for three complete menstrual cycles. However, the axillary pads included in the preparation of the subject samples cam from only five of the fifteen donated cycles. These cycles were selected because they met the following criteria: each was 29.5±2 days in length; the basal body temperature charts were clearly biphasic and presumably ovulatory with thermal rises of twelve or more days, and menstruation occurred within seven days of a full moon. To prepare the stimuli, pads were groups into three-day segments: e.g., all pads from cycle days 1-3 were combined and called "Combined Donor Day 1" (the first day of menstration equals day 1 of the menstrual cycle), all pads in days 4-6 were combined and called "Combined Donor Day 4", all pads in days 7-9 were combined to form "Combined Donor Day 7", and so on. In this fashion, ten separate extracts were prepared, each containing odors from different portions of the menstrual cycle to form the "Donor Cycle" of combined donor days 1, 4, 7, 10, 13, 16, 19, 22, 25 and 28. All pads from each three-day group were placed in a glass column and allowed to soak in doubly distilled ethanol for one hour at room temperature. Fifteen mls of ethanol were used for each pad in the column. After one hour the ethanol extracted materials were allowed to run out the bottom of the column through a PTFE (Teflon) stop cock as the pads were squeezed with a PTFE (Teflon) disc. Approximately two-thirds of all ethanol put on the pads was recovered. The ethanol extracted samples were subsequently frozen at −60° C. until needed.

Subsequently, the steroid content of the extracts were examined and the types of odors present in the separated chromographic effluent were surveyed. Quantitative gas chromotography/mass spectrometry using portions of the individual combined donor days concentrated to a small volume (25-75 ml) was performed employing the "Target Compound Analysis" procedure which is part of the "INCOS" software on the Finnigan/MAT4510GC/MS System. Standard curves of the desired steroids versus a standard (androstane) of constant concentration were first created over a range of concentrations: dehydroepiandrosterone sulphate (DHAS: 1, 5 10 and 25 ng); androsterone sulphate (AS: 1, 5, 10 and 25 ng); androstenol (0.25, 1, 5 and 10 ng); and androstenone (0.25, 1, 5 and 10 ng).

Chromatography was carried out on a 25 m×0.25 mm (O.D.) fused silica column coated with CP SIL-A (Chrompack, Inc., Bridgewater, N.J.), a permanently bonded methyl silica phase with a flow through the column of approximately 3.0 ml/min. All chromatography was done using the following protocol: 100° C. for four minutes, then 4° C. per minute to 300° C.

Figure 1:
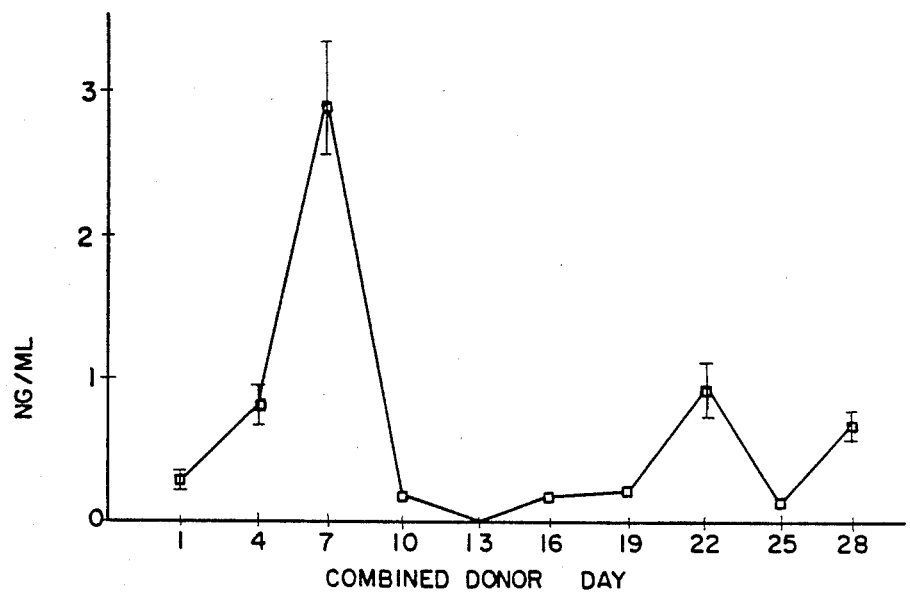
FIG. 1 is a graph of the concentrations in nanograms per milliliter of axillary extract dehydroepiandrosterone. sulphate and androsterone sulphate for samples of axillary extracts pooled from five women donors, as determined over the course of the menstrual cycle.

Analysis of the sulphates noted above are carried out by quantitation of the amount of their major pyrolysis product. See Labows, J.N., Preti, G. Hoelzle, E., Leyden, J. and Kligman, A. M. "Steroid Analysis of Human Apocrine Secretion", *Steroids* 34:249-258 (1979). As can be seen from FIG. 1, the amount of DHAS is markedly elevated in the extract of combined donor day 7, representing combined days 7, 8 and 9. No such elevation is seen for androsterone sulphate, however. The volatile steroid androstenol also rises in concentration at this time, although the levels seens for this compounds are far less that are seen for the sulphates (See FIG. 2). The levels of the compounds reported here are consistent with previous reports examining the steroidal constituents of the axillae. See Labrow, J. N. 1979. "Human Odors—What Can They Tell Us!", Perfumer and Flavorist 4:12-17 and Brooksbank, B. W. L., Brown, R. and Gustafsson, J. A. 1974, "The Detection of 5-androst-16-en-3-ol in Human Male Axillary Sweat", *Experientia* 30:864-865. In the present study, androstenone amounts could not be determined because it elutes closely to the pyrolysis product used for quantitation of androsterone sulfate. However, there appears to be far smaller amounts of androstenone as compared to the androstenol. Studies are currently underway to reexamine freshly concentrated samples of thawed out extract with a different temperature program to allow for resolution of androstenone from the As pyrolysis product so as to determine the levels of androstenone.

It is presently believed that these are the first studies to investigate the concentration changes of axillary secretion steroids across the menstrual cycle. These data indicate that a variation is present, and that secretions from the mid-follicular phase are of particular interest because there appears to be a time of uniquely increased concentrations of dehydroepiandrosterone sulfate and androstenol.

As seen from the above, this knowledge of the behavior of androstenol and dehydroepiandrosterone sulfate facilitates the provision of novel methods for determining the onset of the fertile period of the human female, and for predicting the time of ovulation of that female. While each of the subject compounds exhibits a ten fold mid-follicular phase peak, dehydroepiandrosterone sulfate exhibits more than a fifty fold increase over the base level detected immediately following cessation of menses.

The present invention also provides a novel family planning (birth control or intercourse timing) method wherein the aforementioned changes in concentration of androstenol and/or dehydroepiandrosterone sulfate may be monitored by beginning at the cessation of menses until a first peak in the concentration of at least one of said compounds indicates the onset of the fertile period. Beginning no later than two days after the detection of this peak, and preferably beginning immediately at the time of detection of this peak, the woman should begin to avoid or seek exposure to fertilization in accordance with conceptual planning. Such avoidance should continue until about one day following the expected time of ovulation. If preferred, methods for determining the time of ovulation may be employed, which include clinical methods such as the basal body temperature method, or chemical methods, such as the determination of a peak in the concentration of at least one compound which is indicative of the time of ovulation. Such compounds include a peak in the circulating blood levels of luteinizing hormone, a peak in the concentration of dodecanol in saliva, a peak in certain volatile sulfur containing compounds in mouth air, a peak in the concentration of lactic acid, acetic acid and urea found in vaginal secretions, or peaks in other compounds which are known to be indicative of ovulation.

By using the birth control method of the present invention, contraceptive methods, such as abstinence; contraceptive materials, such as spermicidal foams; or contraceptive devices, such as condoms or diaphragms, need be used for only a portion of the overall menstrual cycle. The reliability of these methods may be further improved by regulating the menstrual cycle of the human female by exposing her nasal region to at least a portion of the axillary secretions of a human donor. As described in the aforementioned related patent applications such axillary secretions may include axillary secretions of at least one human male to thereby induce menstrual cycles having expected lengths of 29.5 ±three days. Alternatively, axillary secretions of at least one other human female exhibiting expected menstrual cycle lengths of 29.5 ±three days may be applied for a similar purpose, when applied in synchrony, or to disrupt the treated female's menstrual cycle to decrease the probability of pregnancy, when applied in an asynchronous manner. Alternatively, the axillary secretions may be collected from a human female exhibiting a shortened luteal phase (less than eleven days) for the purpose of driving the treated female's menstrual cycle towards a presumptively infertile length.

Accordingly, novel methods for improving the reliability of birth control methods relying on the sporadic use of contraceptive methods, materials or devices during a portion of a menstrual cycle of a human female are provided which comprise the step of exposing the nasal region of the human female to an axillary secretion of another human for a duration and in an amount sufficient to adjust the length of the menstrual cycle of said human female to improve the predictability of the presumptive fertile period, thereby facilitating improved reliability of the aforementioned contraceptive methods, materials or devices.

What is claimed is:

1. A birth control method comprising the steps of:
   (a) determining the onset of the fertile period of a human female by monitoring the variation in concentration in the axillary secretions of said female of a compound selected from the group consisting of androstenol and a dehydroepiandrosterone, by beginning said monitoring at the cessation of menses until a first significant increase in a concentration of at least one of said compounds indicates the onset of the fertile period; and
   (b) causing said human female to avoid exposure to fertilization beginning from about that time until at least about 1 day following the expected time of ovulation.

2. The method of claim 1 wherein said dehydroepiandrosterone is dehydroepiandrosterone sulfate.

3. The method of claim 1 wherein said monitored compound is androsterone.

4. The method of claim 1 wherein said monitored compound is dehydroepiandrosterone.

5. The method of claim 1 wherein said method further comprises the step of determining the presumptive time of ovulation.

6. The method of claim 5 wherein said step of determining the time of ovulation is performed using the basal body temperature method.

7. The method of claim 5 wherein said step of determining ovulation is performed by determining a peak in the concentration of at least one compound, the peak of which is indicative of the time of ovulation 8. The invention of claim 7 wherein said peak is a peak in luteinizing hormone.

9. The method of claim 7 wherein said peak is a peak in the concentration of dodecanol in said human female's saliva.

10. The method of claim 7 wherein said peak indicative of ovulation is a peak in the concentration of a compound found in vaginal secretions, said compound being selected from the group consisting of lactic acid, acetic acid, and urea.

11. The method of claim 7 wherein said peak is a peak of a volatile sulfur compound present in mouth air.

* * * * *